US009208774B2

(12) United States Patent
Hardell

(10) Patent No.: US 9,208,774 B2
(45) Date of Patent: Dec. 8, 2015

(54) ADAPTIVE VIBRATION DAMPING MECHANISM TO ELIMINATE ACOUSTIC NOISE IN ELECTRONIC SYSTEMS

(71) Applicant: Apple Inc., Cupertino, CA (US)

(72) Inventor: David A. Hardell, San Jose, CA (US)

(73) Assignee: Apple Inc., Cupertino, CA (US)

( * ) Notice: Subject to any disclaimer, the term of this patent is extended or adjusted under 35 U.S.C. 154(b) by 319 days.

(21) Appl. No.: 13/861,596

(22) Filed: Apr. 12, 2013

(65) Prior Publication Data

US 2014/0307889 A1 Oct. 16, 2014

(51) Int. Cl.

| | |
|---|---|
| ***A61F 11/06*** | (2006.01) |
| ***G10K 11/16*** | (2006.01) |
| ***H03B 29/00*** | (2006.01) |
| ***G10K 11/178*** | (2006.01) |
| *H04R 25/00* | (2006.01) |

(52) U.S. Cl.

CPC ............ *G10K 11/1782* (2013.01); *H04R 25/45* (2013.01); *G10K 2210/129* (2013.01); *G10K 2210/3026* (2013.01); *G10K 2210/3028* (2013.01); *G10K 2210/3214* (2013.01); *H04R 25/453* (2013.01)

(58) Field of Classification Search

CPC .............. G10K 11/16; G10K 11/1782; G10K 2210/129; G10K 2210/3026; G10K 2210/3028; G10K 2210/3214; H04R 3/02; H04R 25/45; H04R 25/453; H04R 2225/49

USPC .................................... 381/71.11, 73.1, 94.9

See application file for complete search history.

(56) References Cited

U.S. PATENT DOCUMENTS

| | | | | |
|---|---|---|---|---|
| 5,422,782 | A | 6/1995 | Hernandez et al. | |
| 7,428,717 | B1 | 9/2008 | Duong | |
| 7,898,818 | B2 | 3/2011 | Kehoe | |
| 8,149,565 | B2 | 4/2012 | Lee et al. | |
| 2004/0183147 | A1* | 9/2004 | Togashi et al. | 257/414 |
| 2009/0147456 | A1 | 6/2009 | Kim et al. | |
| 2010/0033938 | A1* | 2/2010 | Kitagawa et al. | 361/748 |
| 2012/0126157 | A1* | 5/2012 | Beck et al. | 251/129.05 |
| 2013/0055810 | A1* | 3/2013 | Yanagisawa et al. | 73/504.12 |
| 2014/0160622 | A1* | 6/2014 | Chung et al. | 361/301.4 |
| 2014/0174806 | A1* | 6/2014 | Park et al. | 174/260 |

* cited by examiner

*Primary Examiner* — Khai N Nguyen

(74) *Attorney, Agent, or Firm* — Downey Brand LLP

(57) ABSTRACT

A system to eliminate acoustic noise caused by a first Multi-Layer Ceramic Capacitor (MLCC) array positioned on a printed circuit board (PCB) is disclosed. The first MLCC array generates a first vibration responsible for the acoustic noise in response to receiving a varying input voltage. A third MLCC array senses the first vibration and generates a feedback signal. An adaptive filter then uses the feedback signal to generate an output signal that is used by a second MLCC to generate a second vibration that acts as a counter to dampen the first vibration. Because the input voltage signal is varying in time, the adaptive filter continually samples the varying input voltage and the feedback signal to generate the output signal that minimizes the acoustic noise. The second and third MLCC arrays are selectively positioned and oriented on the PCB for optimum performance.

20 Claims, 10 Drawing Sheets

400

ADAPTIVE VIBRATION DAMPING MECHANISM TO ELIMINATE ACOUSTIC NOISE IN ELECTRONIC SYSTEMS

FIELD OF THE DESCRIBED EMBODIMENTS

The described embodiments relate generally to methods and systems for eliminating or reducing acoustic noise in electronic systems, and more particularly to methods and systems for using an adaptive vibration damping mechanism for eliminating or reducing acoustic noise from a printed circuit board (PCB) caused by Multi-Layer Ceramic Capacitors (MLCC) or other similar components containing piezoelectric material.

BACKGROUND

Electronic systems commonly use Multi-Layer Ceramic Capacitors (MLCC) for such tasks as decoupling power supplies, or filtering signals. The ceramic material in the MLCC has a piezoelectric property which causes it to expand and contract in response to applied electric fields. This expansion and contraction can cause the components to vibrate. These components are very small, so the vibration of an individual part may not be significant. However, when there is an array of these parts vibrating synchronously, the effect is increased. Further, once the parts are fixed to a large, flexible substrate, as is the case when they are soldered down to a printed circuit board (PCB), the vibration is amplified further. What might have been a benign problem becomes a serious problem, particularly when the driving voltage varies at a frequency in the audible range. The problem may be manifested as a high pitched squealing noise coming from the product.

To combat this problem, system engineers and component engineers have focused on MLCC package modifications to minimize the coupling to the PCB, and on placement of the MLCCs, sometimes in pairs, to partially cancel or otherwise reduce the amplification of the vibration. Modifications to the package can lead to degraded performance of the capacitor when the mechanical changes add series impedance. Creative layout solutions only go so far in dampening the acoustic noise, and in many cases require compromises in electrical performance or space allocation to implement them.

Therefore, what is desired is a method or system to eliminate or greatly reduce acoustic noise in electronic systems caused by MLCC or other similar components containing piezoelectric material.

SUMMARY OF THE DESCRIBED EMBODIMENTS

The approach described here is to sense the vibration caused by the excitation of the Multi-Layer Ceramic Capacitors (MLCCs) in response to receiving a varying input voltage, and then to drive a dedicated Multi-Layer Ceramic Capacitor (MLCC), or an array of MLCCs, that acts as a counter actuator to dampen or remove the vibration. In one embodiment, an array can be one or more MLCCs of one or more package sizes and of one or more capacitance values. In one embodiment, the approach can also be applied to other similar, but non-MLCC, components that contain piezoelectric materials. Since both the input voltage signal driving the MLCC and the transfer function that characterizes the conversion from voltage to sound pressure (the audible noise) are varying in time, the approach described here is an adaptive approach. This means that the damping signal is generated using an adaptive filter, which changes dynamically in response to the varying input signal and feedback signal. In this regard, the feedback signal is a proxy for the acoustic noise. The approach described here can involve three MLCC arrays positioned on a printed circuit board (PCB). A first MLCC array generates a first vibration responsible for the acoustic noise in response to receiving a varying input voltage. A third MLCC array senses the first vibration, while a second MLCC array generates a second vibration to cancel out or reduce the first vibration. Therefore, the second and third MLCC arrays can be selectively positioned and oriented on the PCB to maximize sensing and cancellation of the first vibration. As an example, the second and third MLCC can be placed near the point of maximum flexure of the PCB.

In one embodiment, a system to eliminate an acoustic noise caused by a first MLCC array positioned on a PCB is disclosed. The system includes a first MLCC array, a third MLCC array, an adaptive filter, and a second MLCC array. The first MLCC array is positioned on the PCB and configured to generate a first vibration in response to receiving a varying input voltage. The first vibration is causing the acoustic noise. The third MLCC array is positioned on the PCB and configured to sense the first vibration and generate a feedback signal. The adaptive filter is configured to use the varying input voltage and the feedback signal to generate an output signal. The second MLCC array is positioned on the PCB and configured to use the output signal to generate a second vibration that acts as a counter to dampen the first vibration. In one embodiment, the adaptive filter continually samples the varying input voltage and the feedback signal to generate the output signal that minimizes the acoustic noise. In one embodiment, the third MLCC array is positioned near a point of maximum flexure of the PCB. In one embodiment, the third MLCC array is oriented to measure all meaningful modes of the first vibration. In one embodiment, the third MLCC array includes more than one independent MLCC sensors, and the more than one independent MLCC sensors are placed at different locations, or in different orientations, or both. In one embodiment, the second MLCC array is positioned near a point of maximum flexure of the PCB. In one embodiment, the second MLCC array includes more than one independent MLCCs, and the more than one independent MLCCs are placed at different locations, or in different orientations, or both. In one embodiment, the second MLCC array is placed near the first MLCC array. In one embodiment, the third MLCC array is not a dedicated sensor capacitor array, and the third MLCC array is configured to perform other functions. In one embodiment, the second MLCC array is not dedicated to generating the second vibration that acts as a counter to dampen the first vibration, and the second MLCC array is configured to perform other functions.

In one embodiment, a system to eliminate an acoustic noise caused by a first electronic component containing piezoelectric material is disclosed. The system includes a first electronic component containing piezoelectric material, a third electronic component, an adaptive filter, and a second electronic component containing piezoelectric material. The first component is configured to generate a first vibration in response to receiving a varying input voltage. The first vibration is causing the acoustic noise. The third component is configured to sense the first vibration and generate a feedback signal. The adaptive filter is configured to use the varying input voltage and the feedback signal to generate an output signal. The second component is configured to use the output signal to generate a second vibration that acts as a counter to dampen the first vibration. In one embodiment, the adaptive filter continually samples the varying input voltage and the feedback signal to generate the output signal that minimizes the acoustic noise. In one embodiment, the third electronic component is selected from the group consisting of a strain gauge, a microphone, and an electronic device containing piezoelectric material. In one embodiment, the first electronic component is positioned on a PCB. In one embodiment, the second electronic component is a part of the PCB.

In one embodiment, a method to eliminate an acoustic noise caused by a first MLCC positioned on a PCB is disclosed. The method includes sensing, with a third MLCC, a first vibration and generating a feedback signal. The first vibration is caused by an excitation of the first MLCC in response to receiving a varying input voltage. The first vibration is causing the acoustic noise. The method also includes generating, with an adaptive filter using the feedback signal, an output signal that is used by a second MLCC to generate a second vibration. The method further includes generating, with the second MLCC using the output signal, the second vibration that acts as a counter to dampen the first vibration. In one embodiment, the adaptive filter continually samples the varying input voltage and the feedback signal to generate the output signal that minimizes the acoustic noise. In one embodiment, the adaptive filter periodically samples the varying input voltage and the feedback signal at a fixed time interval. In one embodiment, the varying input voltage changes over time in frequency, phase, and amplitude. In one embodiment, the adaptive filter is a digital filter. In one embodiment, the adaptive filter is a Finite Impulse Response (FIR) linear digital filter. In other embodiments, the adaptive filter can be an Infinite Impulse Response (IIR) filter, an adaptive analog filter, a nonlinear adaptive filter, or a Kalman filter.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

DETAILED DESCRIPTION OF SELECTED EMBODIMENTS

Representative applications of methods and apparatus according to the present application are described in this section. These examples are being provided solely to add context and aid in the understanding of the described embodiments. It will thus be apparent to one skilled in the art that the described embodiments may be practiced without some or all of these specific details. In other instances, well known process steps have not been described in detail in order to avoid unnecessarily obscuring the described embodiments. Other applications are possible, such that the following examples should not be taken as limiting.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

The approach described here is to sense the vibration caused by the excitation of the MLCCs, and then to drive a dedicated MLCC, or an array of MLCCs, that acts as a counter actuator to dampen or remove the vibration. In one embodiment, the vibration can be caused by the excitation of other similar, but non-MLCC, components. In another embodiment, other similar, but non-MLCC, components can act as a counter actuator to dampen or remove the vibration. The ceramic material in the MLCC has a piezoelectric property which is inverse-dual, meaning that a changing electric field can cause them to vibrate, and conversely, a physical vibration can cause an electric field to be generated in them. Therefore, in one embodiment, these similar, but non-MLCC, components can include piezoelectric materials. In one embodiment, MLCC sensors can be used for the feedback. In another embodiment, non-MLCC sensors (e.g. a strain gauge or a microphone) can be used for the feedback.

Since neither the characteristics of the driving signal (the excitation voltage on the MLCC), nor the transfer function from voltage to sound pressure (the audible noise) is fixed, but rather both vary with time, the approach described here is an adaptive approach. This means that the damping signal is generated with the aid of an adaptive filter which changes dynamically in response to the varying input signal and feedback signal, which is a proxy for the acoustic noise.

Figure 1:
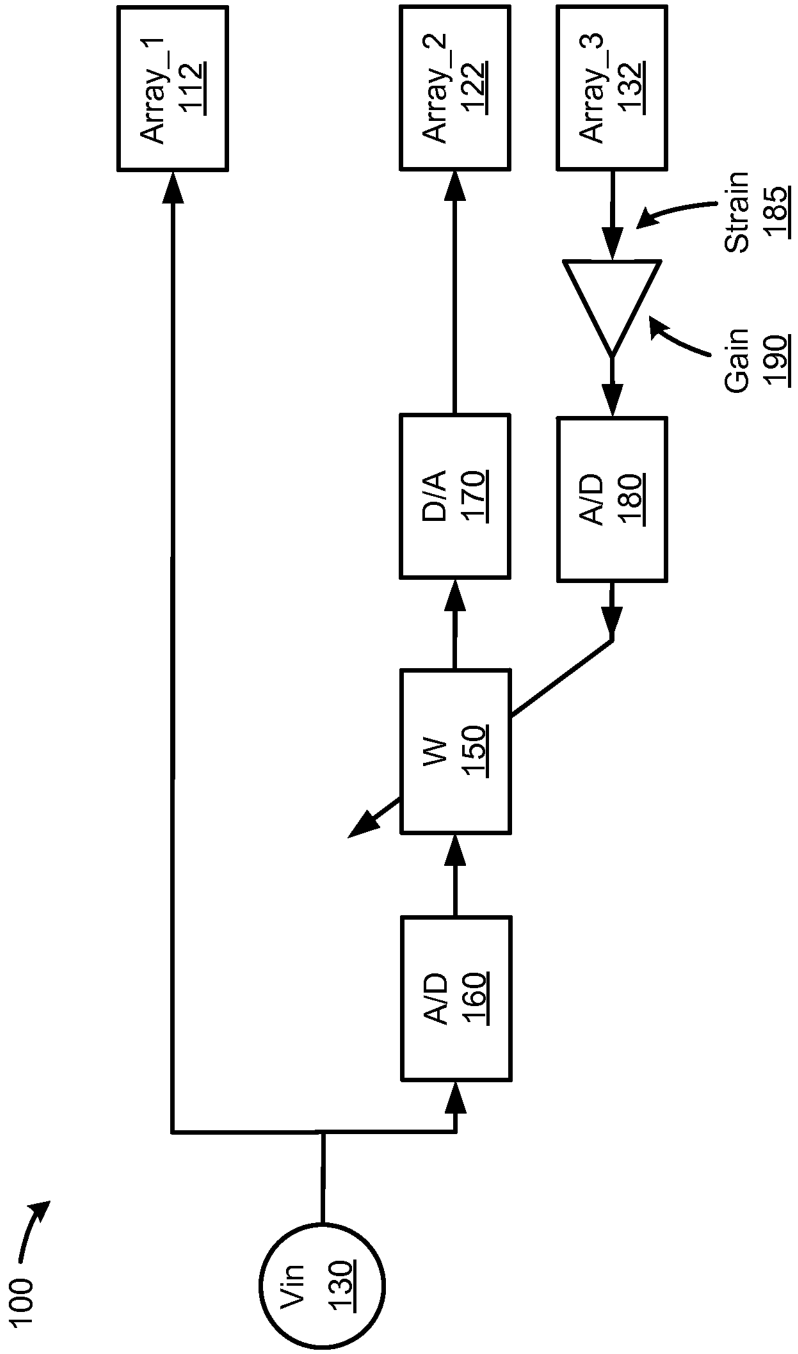
FIG. 1 illustrates an embodiment of a functional electronic system with an adaptive vibration damping mechanism to eliminate or reduce acoustic noise associated with an MLCC array on a PCB.

FIG. 1 illustrates an embodiment of a functional electronic system 100 with an adaptive vibration damping mechanism to eliminate or reduce acoustic noise. This embodiment utilizes an all-digital implementation for adaptive filter 150 (labeled as W). Accordingly, Analog-to-Digital Converter (A/D) 160 and 180 convert analog signals into digital signals for input into adaptive filter 150, while Digital-to-Analog Converter (D/A)170 accepts a digital output signal from adaptive filter 150 for conversion to an analog signal. There is also an amplifier 190 that boosts strain signal 185 for input into A/D 180, because the strain signal 185 can be very weak. In some embodiments, there may (or may not) also be a driver on the output of the D/A 170. In some embodiments, there may (or may not) also be a filter on the input of the A/D 160. In one embodiment, this filter can be low pass or band pass. A band pass filter can be used, for example, to ensure that the input signal goes to zero when the voltage variation is outside the relevant acoustic range.

The functional electronic system 100 can have an array 112 of MLCC components configured to receive a varying input voltage Vin 130, whose variation is in the acoustic frequency range. In FIG. 1, array 112 of MLCC components is labeled as Array_1. The voltage characteristics of Vin 130 do not have to be fixed, but can change over time in frequency, phase, and amplitude. In one embodiment, the MLCC array 112 can be coupled to a PCB substrate, and the vibration of the MLCC array 112 can cause the PCB to vibrate in the acoustic frequency range.

In one embodiment, a large MLCC package, or MLCC array 132, can be used as a strain sensor. In FIG. 1, array 132 is labeled as Array_3. In one embodiment, the MLCC array 132 can be placed near the point of maximum strain. In one embodiment, the MLCC array 132 can be oriented to experience maximum flexure of the PCB. In one embodiment, the PCB can be characterized for the location and orientation that provides for the maximum flexure of the PCB and the maximum strain on the MLCC. In one embodiment, the point on the PCB providing for the maximum flexure of the PCB corresponds to the point furthest away from the fixed PCB mounting points. In a rectangular shaped PCB, where the fixed PCB mounting points are at the four corners, this point of maximum flexure would be the center of the rectangle, which is the furthest point from all four mounting points. In one embodiment, the MLCC array 132 can be oriented so as to measure all the meaningful modes of vibration. A large package can have better sensitivity than a small package. However, a smaller package can also be used. If necessary, more than one independent MLCC sensor can be placed, at different locations, or different orientations, or both.

FIGS. 2A to 2E show how MLCC array 132 (Array_3) can be placed, at different locations, or different orientations, or both. Regarding location, for example, MLCC array 132 (Array_3) can be placed near the center of the PCB, as shown in embodiment 200A of FIG. 2A. MLCC array 132 (Array_3) can be placed near an edge of the PCB, as shown in embodiment 200B of FIG. 2B. MLCC array 132 (Array_3) can be placed near MLCC array 112 (Array_1), as shown in embodiment 200C of FIG. 2C. Regarding orientation, for example, one MLCC sensor can be oriented to measure vibration along the x-axis, while another MLCC sensor can be oriented to measure vibration along the y-axis, as shown in embodiment 200D of FIG. 2D. MLCC sensor also can be oriented to measure vibration along any axis that is rotated by a given angle from the x-axis. One such angle can be 45 degrees, as shown in embodiment 200E of FIG. 2E. For a rectangular shaped PCB, the x-axis can correspond to the longer side of the rectangle, while the y-axis can correspond to the shorter side of the rectangle.

Figure 2A:
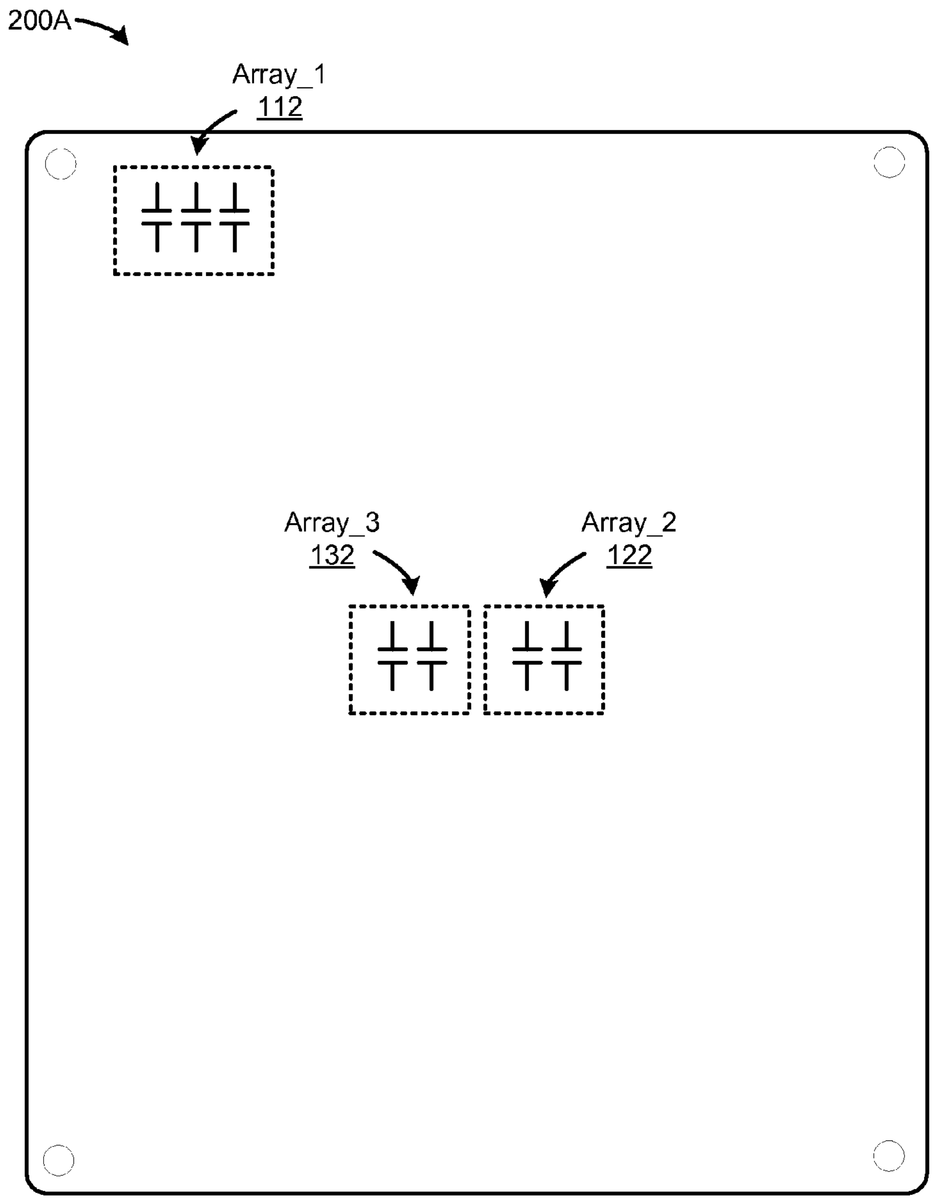
FIGS. 2A-2E illustrate different embodiments of placing and orienting three MLCC arrays on a rectangular shaped PCB for the purpose of eliminating or reducing acoustic noise associated with one of the MLCC array.
Figure 2B:
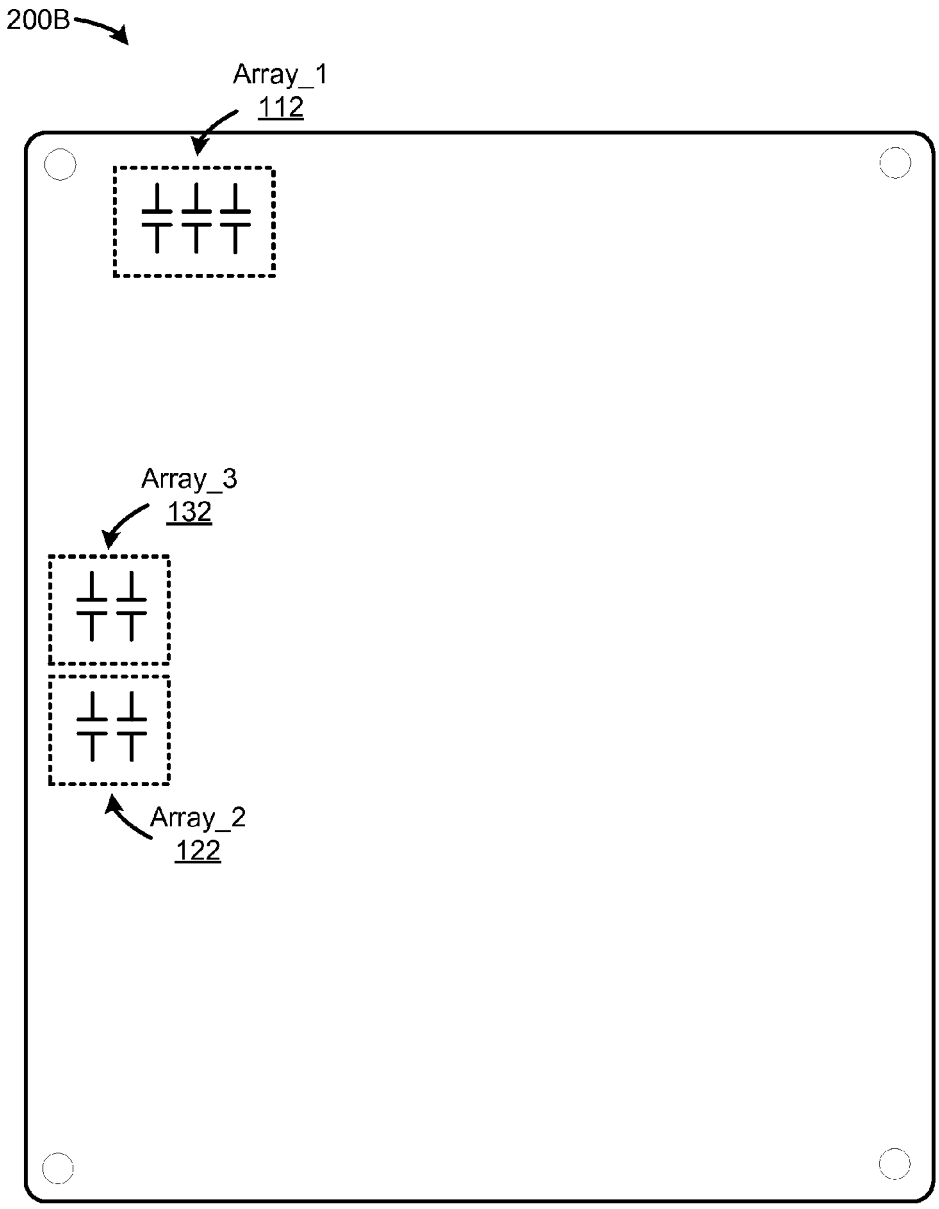
Figure 2C:
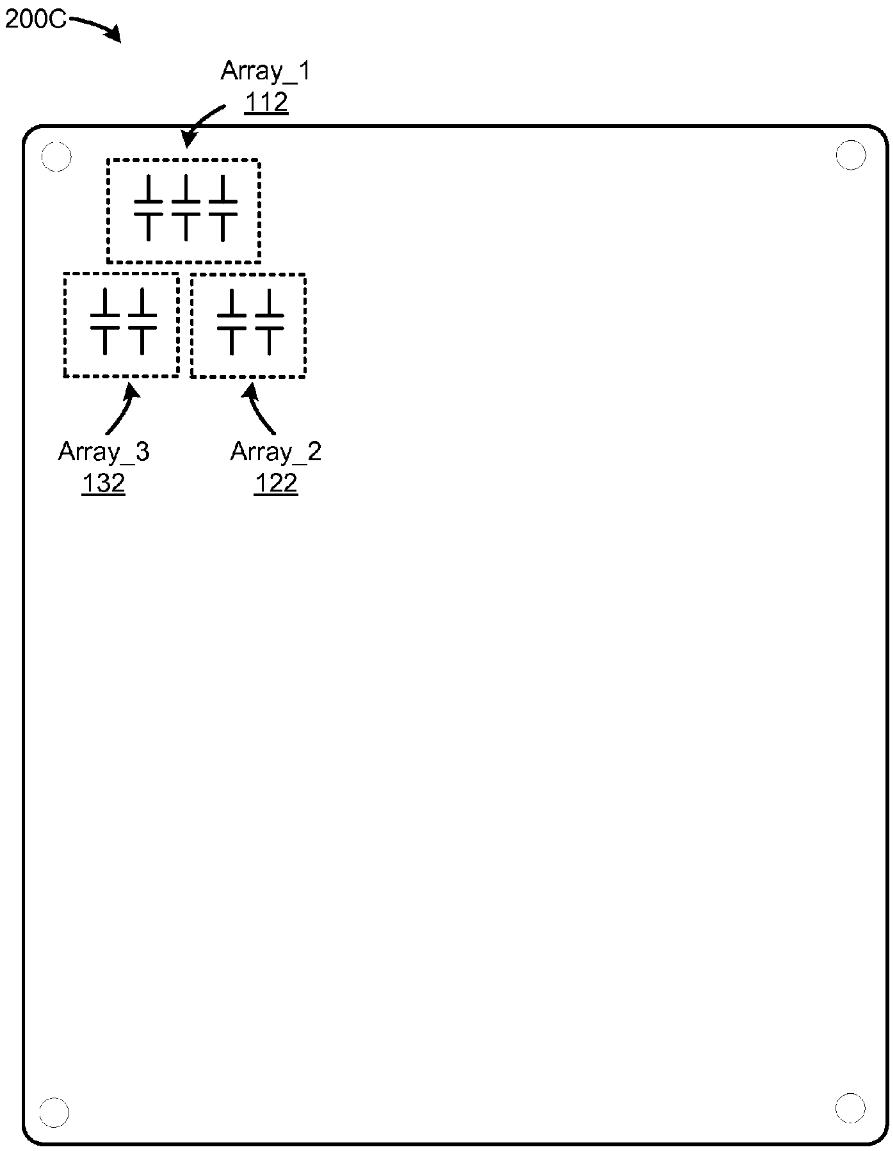
Figure 2D:
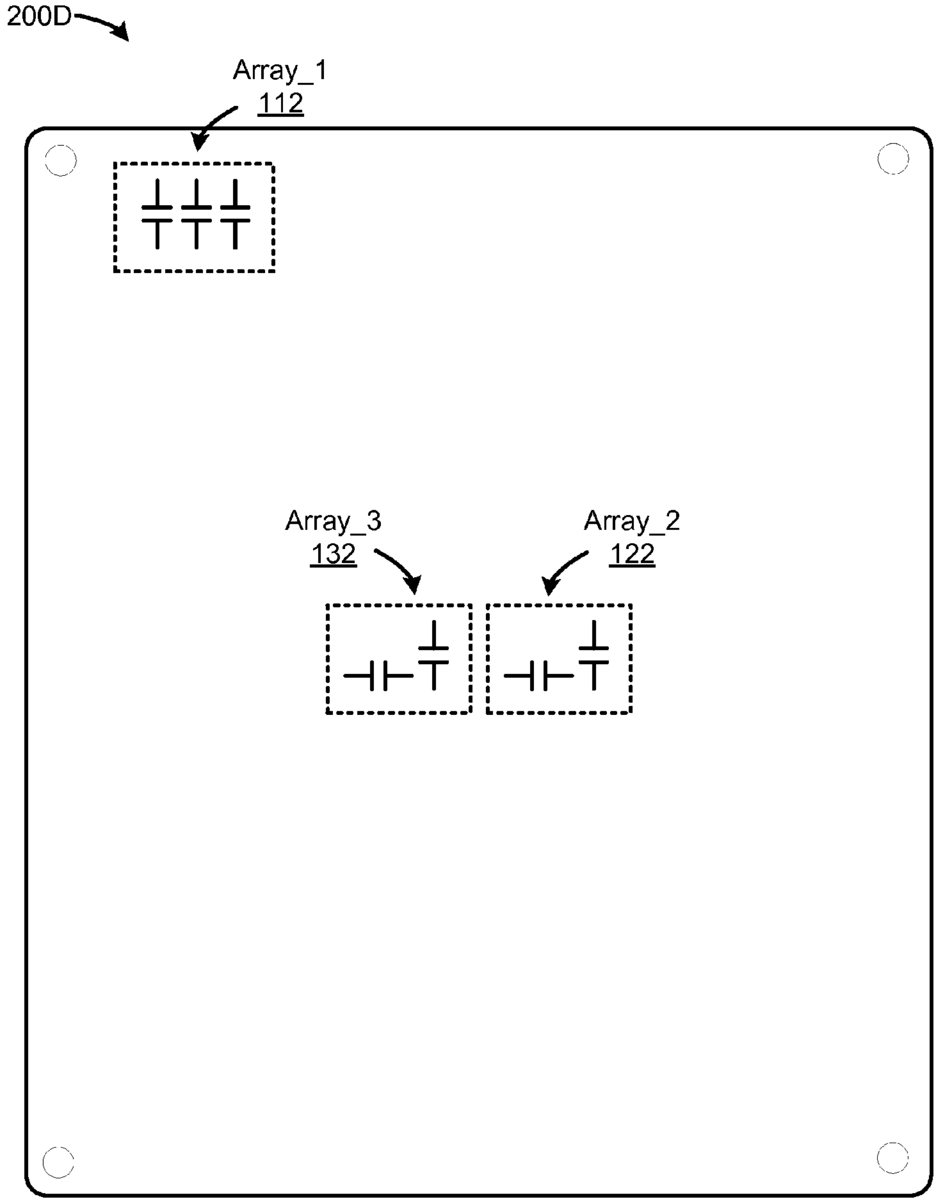
Figure 2E:
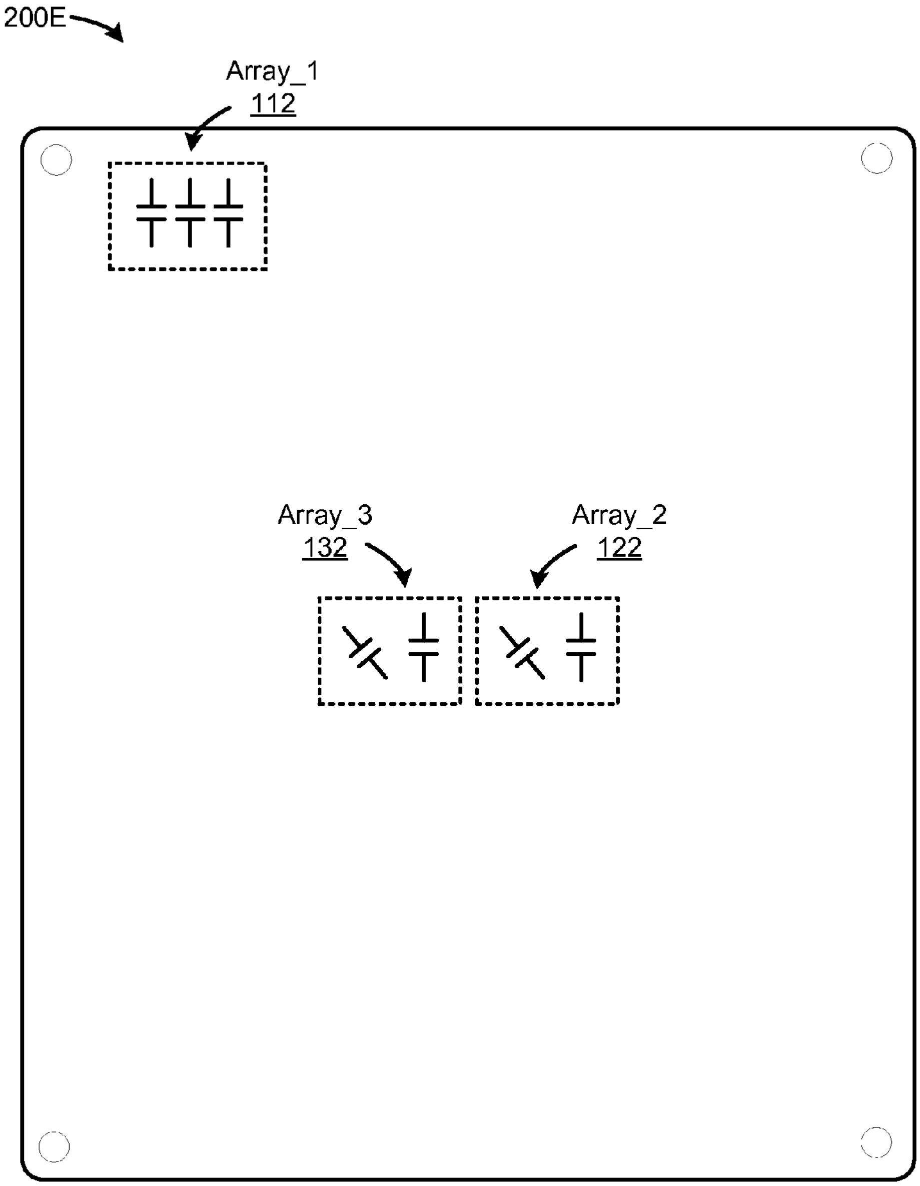

A complimentary array 122 of MLCC can be used to generate a second vibration that acts as a counter to dampen the first vibration associated with array 112 of MLCC. In FIGS. 1 and 2A-2E, array 122 is labeled as Array_2. The MLCC Array_2 and Array_3 can be equivalent packages (all 0603, for example), or they can be of different package sizes (0603 and 0805, for example). There can be advantages to either approach. FIG. 2A shows embodiment 200A of a rectangular shaped PCB, where Array_2 is placed adjacent to, and oriented equivalently to, Array_3. FIG. 2A also shows that Array_2 and Array_3 are placed at a location on the PCB that is far away from Array_1. Array_2 and Array_3 can be placed near the center of the PCB, because the center of the PCB can be the point of maximum flexure. Such a placement can allow for maximum sensing and cancellation of the vibration arising from Array_1.

A useful property of piezoelectric materials is that they are inverse-dual, meaning that a changing electric field can cause them to vibrate, and conversely, a physical vibration can cause an electric field to be generated in them. Electronic system 100 takes advantage of this property with the MLCCs belonging to Array_3, which is also labeled as array 132. An adaptive system senses the voltage created across the Array_3 MLCCs as the flexing PCB puts strain on the MLCC packages. This voltage acts as a feedback signal to an adaptive control system.

In summary, both FIGS. 1 and 2A-2E illustrate three separate MLCC arrays. The first array, Array_1, includes functional MLCCs on PCB, which can cause vibration and acoustic noise in response to voltage changes in Vin 130. The third array, Array_3, includes MLCCs on PCB, which can be used to measure strain as the PCB flexes. The second array, Array_2, includes MLCCs on PCB, which can be used to flex the PCB in opposition to the vibration and acoustic noise of Array_1.

Figure 3:
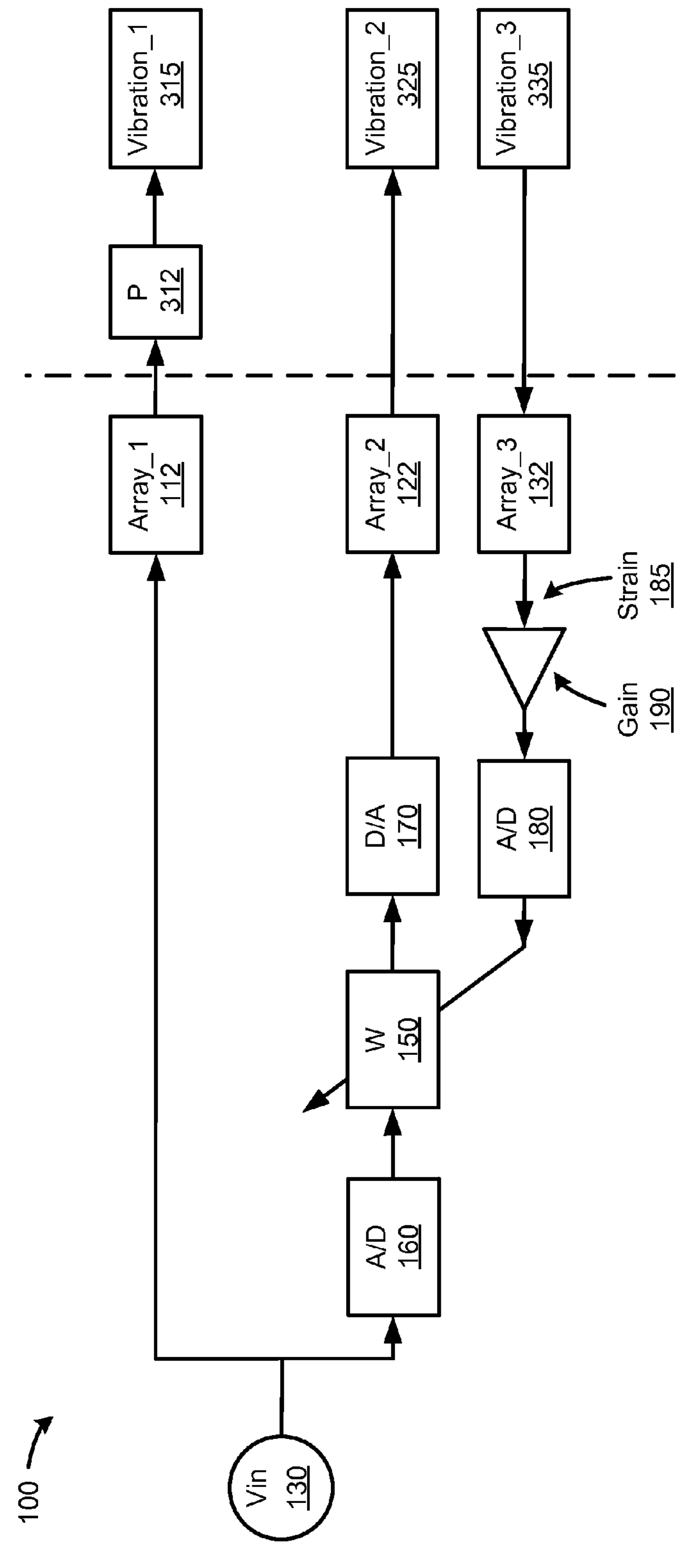
FIG. 3 illustrates the functional electronic system of FIG. 1 together with the vibrations associated with the various MLCC arrays and a transfer function.

FIG. 3 shows that a first vibration 315 (i.e., Vibration_1) is associated with MLCC array 112 (i.e., Array_1). Similarly, a second vibration 325 (i.e., Vibration_2) is associated with MLCC array 122 (i.e., Array_2), and a third vibration 335 (i.e., Vibration_3) is associated with MLCC array 132 (i.e., Array_3). Array_2 is generating a second vibration 325 to flex the PCB in opposition to the vibration and acoustic noise of Array_1. Therefore, first vibration 315 is being dampened or "reduced" by second vibration 325 to form third vibration 335. In other words, Vibration_1 minus Vibration_2 equals Vibration_3 (i.e., Vibration_1−Vibration_2=Vibration_3). FIG. 3 further shows that block P 312 represents the transfer function from capacitor voltage (Vin) on MLCC Array_1 to the resulting Vibration_1 (315). Additionally, in one embodiment, the vibrations (i.e., Vibration_1, Vibration_2, and Vibration_3) can include both the vibrations of the MLCC array itself and the vibrations of the PCB, since the vibrations are amplified further when the MLCC arrays are soldered down to a PCB.

Figure 4:
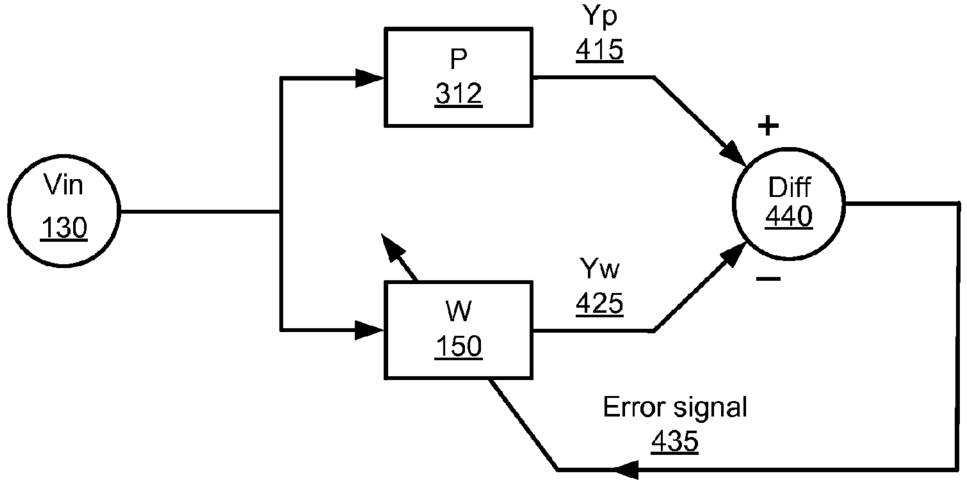
FIG. 4 illustrates a high level block diagram of an adaptive system configured to eliminate or reduce acoustic noise.

FIG. 4 illustrates a high level block diagram of an adaptive system 400 that can be used to eliminate or reduce acoustic noise caused by a first MLCC array positioned on a PCB. In FIG. 4, block P 312 represents the transfer function from capacitor voltage (Vin) on MLCC Array_1 to PCB flexure (i.e., PCB vibrations). Block W 150 represents the adaptive filter 150, which takes as inputs the same Vin that drives the Array_1 MLCCs, and also the feedback signal generated by Array_3 MLCCs for sensing board flexure. The output of block W drives the Array_2 MLCCs, which themselves cause a directed flexure of the PCB. In FIG. 4, the output of the W adaptive filter 150 (Yw 425) is subtracted from the output of the P transfer function (Yp 415) by component Diff 440 to form an error signal 435, which is then used to change the W adaptive filter 150. The W adaptive filter 150, in turn, will try to drive the coefficients in the filter in order to minimize the error signal 435. Once the error signal 435 becomes zero or close to zero, then output Yw 425 will be equal to output Yp 415. In other words, the algorithm running in the W adaptive filter is trying to minimize the error signal 435 ($e$), where e=Yp−Yw, and the minimum error signal 435 is achieved when Yp=Yw. Turning back to FIG. 3, the same input voltage Vin 130 is driving both the MLCC Array_1 and W adaptive filter 150, while the error signal 435 corresponds to strain signal 185, which measures the PCB flexure using MLCC Array_3. Accordingly, the W adaptive filter 150 is being modified to achieve an output that can generate a Vibration_2 which can cancel out Vibration_1. When Vibration_2 cancels out Vibration_1, Vibration_3 equals zero. There are no more vibrations and, accordingly, no more acoustic noises.

The adaptive vibration damping mechanism can be implemented in multiple ways. The signals can be analog, and the algorithm can be implemented as either analog or digital. Alternatively, the signals can be digitized, and the algorithm implemented digitally, with the output then being converted back to analog to drive the MLCCs. The following description assumes an all-digital implementation, with a digital filter for block W. This all-digital implementation was previously shown in FIG. 1.

The adaptive filter 150, W, is a structure which adjusts its filter coefficients after every digital sample. The adjustment can be made based on any number of algorithms described in the literature: Least Mean Squares (LMS), or Recursive Least Squares (RLS), for example. There are also nonlinear adaptive filtering approaches which can be applied to this problem (the Volterra adaptive filter for example). The simplest embodiment to describe is the LMS filter, which is a gradient descent approach using an FIR (Finite Impulse Response) linear digital filter.

The FIR digital filter operates by first multiplying successively delayed input samples by weight values called coefficients (or tap weights). In one embodiment, the FIR digital filter can have 10 coefficients. These delayed and scaled samples are then summed to generate an output sample. The nature of the digital filter is determined by its impulse response, which is defined by these tap weights, and can be configured for low-pass, high-pass, etc., or can be configured for phase and magnitude adjustments of the input signals. In principle, if the ideal impulse response to use is known in advance, the vibration caused by an MLCC array can be perfectly canceled. When the required impulse response is not known in advance, an algorithm can be used to adaptively attain it.

FIG. 1 shows that the input voltage, Vin 130, is first digitized and then applied, one sample at a time, to the filter block W. The objective of the adaptation algorithm is to drive the evolution of the filter coefficients in a direction which reduces the error signal 435, which is the feedback signal labeled as “strain” 185 in FIGS. 1 and 3. In other words, the algorithm is designed to modify the coefficients so that the PCB flexure is minimized, thereby minimizing the strain signal from the combination of MLCC Array_1 and Array_2.

Figure 5:
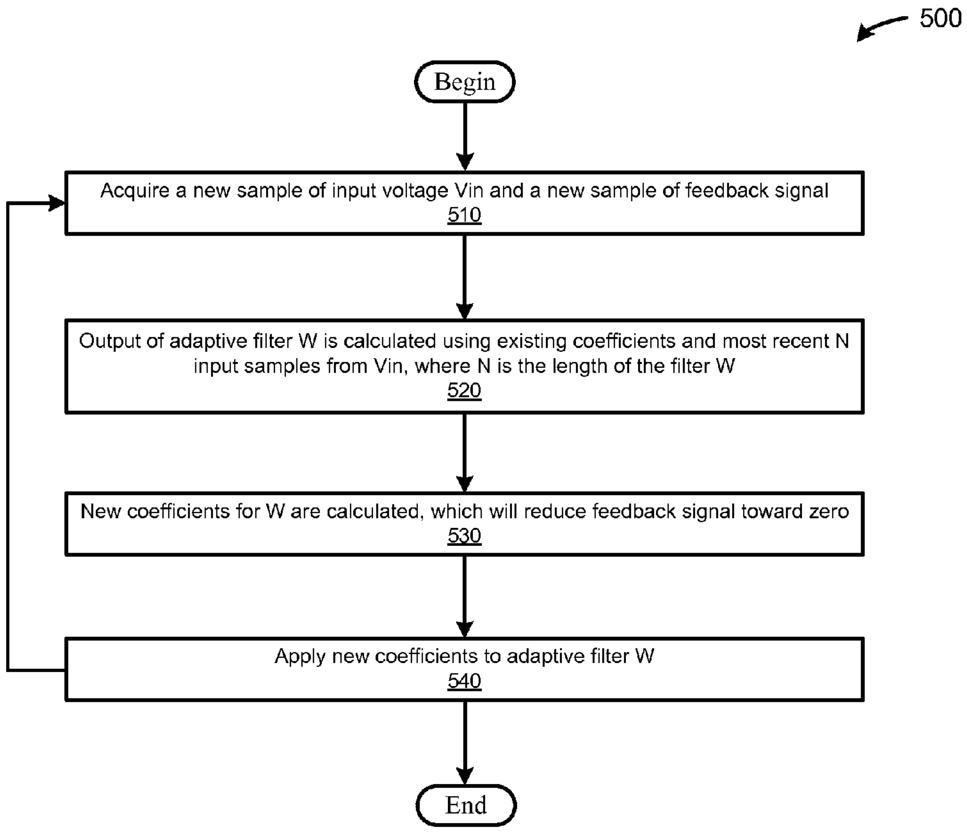
FIG. 5 illustrates a flow chart showing method steps for a process to minimize the acoustic noise by continually sampling the varying input voltage and the feedback signal, where the feedback signal is a proxy for the acoustic noise, according to one embodiment of the invention.

FIG. 5 illustrates a flow chart showing method steps for a process 500 to minimize the acoustic noise by continually sampling the varying input voltage and the feedback signal, where the feedback signal is a proxy for the acoustic noise, according to one embodiment of the invention. Although the method steps of process 500 are described in conjunction with FIGS. 1 and 3, persons skilled in the art will understand that any system configured to perform the method steps, in any order, is within the scope of the invention.

As shown in FIG. 5, the process 500 begins at step 510, where the adaptive filter W 150 acquires a new sample of input voltage Vin 130 and a new sample of feedback signal from Array_3. At step 520, the output of W is first calculated using the existing coefficients and the most recent N input samples from Vin 130, where N is the length of filter W. At step 530, new coefficients for W are calculated, which will reduce the feedback toward zero. At step 540, the new coefficients are applied for adaptive filter W 150. Then the process continues back to step 510, and a new sample of input voltage Vin 130 and a new sample of feedback signal is acquired. This is a dynamic adaptive process, where the adaptive filter W 150 is continually trying to reduce the feedback, which is a proxy for the acoustic noise, toward zero. In one embodiment, the adaptive filter 150 continually samples the varying input voltage and the feedback signal by periodically sampling the varying input voltage and the feedback signal at a fixed time interval. Since the acoustic noises of interest are in the audio range, the sampling rate has to be fast relative to the audio range. In another embodiment, the time interval can be variable. Because there are higher frequency contents in the varying input voltage Vin 130 that exceed the audio range, Vin 130 can be pre-filtered before sampling from A/D 160, which is shown in FIGS. 1 and 3. This pre-filter can be low pass or band pass.

In FIG. 1, the D/A (digital to analog) converter 170 converts the digital output of W to an analog voltage. This analog voltage is then applied to Array_2. The changing electric field on Array_2 MLCCs causes that array to vibrate, but the vibration is driven in a way which acts against the vibration caused by Array_1 MLCCs. Once the filter coefficients for W converge to a steady state solution, the PCB vibration, and hence the acoustic noise, can be almost completely cancelled.

The resulting cancellation may not be perfect, because a nonlinear system (i.e., the transfer function P) is being modeled using a linear filter (i.e., the FIR filter of W). To improve the cancellation, one embodiment of the system can elect to use a more elaborate nonlinear adaptive filter and algorithm for W. However, a nonlinear implementation requires more cost, space, power, and computing resources, as compared to a linear implementation. As such, the simplest linear implementation might be the most attractive option.

In another embodiment, the cancellation can be improved by including an Array_2 and Array_3 for each significant vibration mode in the PCB (selected by physical orientation of the arrays). In the extreme case, there can be an independent W filter and algorithm operating on each mode array set. Alternatively, the sensor inputs can be merged into a single algorithm, which generates multiple outputs.

Figure 6:
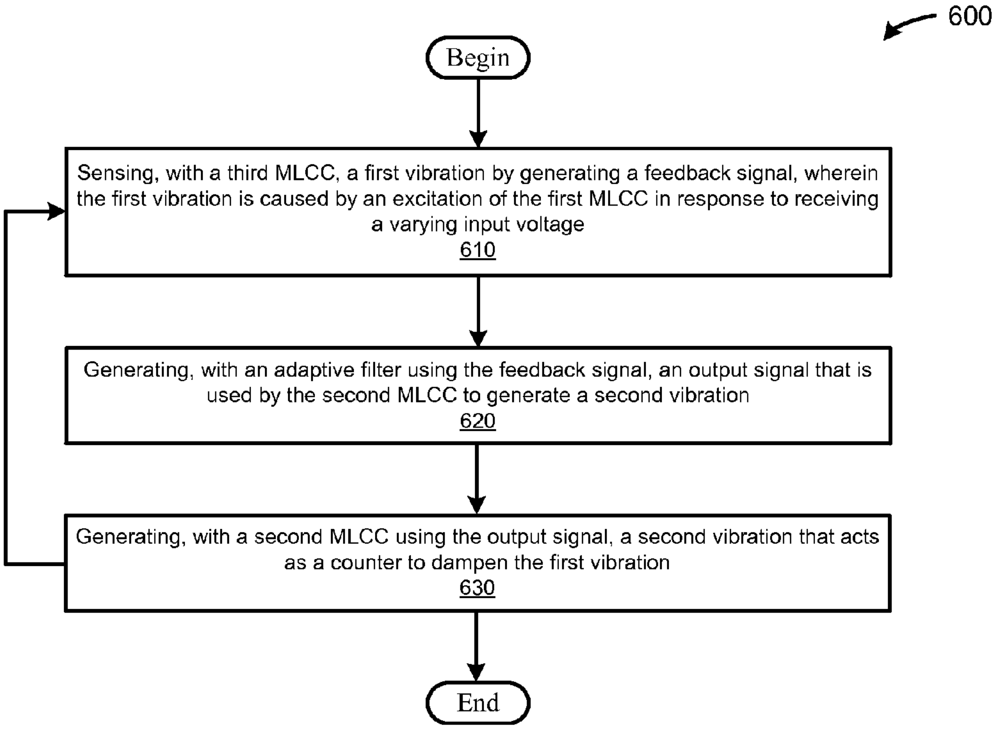
FIG. 6 illustrates a flow chart showing method steps for a method to eliminate an acoustic noise caused by a first MLCC positioned on a PCB, according to one embodiment of the invention.

FIG. 6 illustrates a flow chart showing method steps for a method 600 to eliminate an acoustic noise caused by a first MLCC positioned on a PCB, according to one embodiment of the invention. Although the method steps of method 600 are described in conjunction with FIGS. 1 and 3, persons skilled in the art will understand that any system configured to perform the method steps, in any order, is within the scope of the invention.

As shown in FIG. 6, the method 600 begins at step 610, where a third MLCC senses a first vibration and generates a feedback signal. The first vibration is caused by an excitation of the first MLCC in response to receiving a varying input voltage. The first vibration causes the acoustic noise. At step 620, an adaptive filter 150, using the feedback signal, generates an output signal that is used by the second MLCC to generate a second vibration. At step 630, a second MLCC, using the output signal, generates a second vibration that acts as a counter to dampen the first vibration. After step 630, the method 600 returns to step 610, so that the third MLCC can sample the “new” first vibration (or, more correctly, the combination of the “old” first vibration and the “old” second vibration) to generate a new feedback signal. This is because both the input voltage signal driving the first MLCC and the transfer function that characterizes the conversion from voltage to sound pressure (the audible noise) for the first MLCC are not fixed, but rather varying in time. Therefore, method 600 needs to generate a “new” updated second vibration that will cancel out the first vibration. To generate a new updated second vibration, steps 610, 620, and 630 must be repeated. In other words, as method 600 repeats itself, the adaptive filter 150 is continually sampling the varying input voltage and the feedback signal to generate the output signal that can minimize the acoustic noise.

In summary, this disclosure describes a method of actively driving an MLCC array to dampen the vibrations of a PCB in an electronic product. The features include:

a) using an MLCC array as an actuator to counter vibrational forces, b) using an MLCC array as a piezoelectric sensor to create a proxy for acoustic noise, and c) using adaptive techniques to dynamically derive the impulse response of the dampening signal, and d) implementing an adaptive system in a novel way.

The present implementation of an adaptive system is novel, because vibrations (i.e., physical forces) are "added" or "combined" to create the error signal. In particular, the error signal (i.e., strain signal 185 in FIGS. 1 and 3) is generated by first converting an electrical output (i.e., output from adaptive filter 150) to a physical force (i.e., vibration_2, which is generated by driving MLCC array 122 through a piezoelectric material). Then this physical force (i.e., vibration_2) is combined with an existing force (i.e., vibration_1) on the PCB in real time. The system senses the result of that combination (i.e., vibration_3) in order to create an error signal (i.e., strain signal 185) representing the net flexure on the PCB.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A system to eliminate an acoustic noise caused by a first multi-layer ceramic capacitor (MLCC) array positioned on a printed circuit board (PCB), the system comprising:

the first MLCC array positioned on the PCB and configured to generate a first vibration in response to receiving a varying input voltage, the first vibration causing the acoustic noise;

a second MLCC array positioned on the PCB and configured to sense the first vibration and generate a feedback signal;

an adaptive filter configured to use the varying input voltage and the feedback signal from the second MLCC array to generate an output signal; and a third MLCC array positioned on the PCB and configured to use the output signal to generate a second vibration that acts to dampen the first vibration.

2. The system of claim 1, wherein the adaptive filter continually samples the varying input voltage and the feedback signal to generate the output signal that minimizes the acoustic noise.

3. The system of claim 1, wherein the second MLCC array is positioned near a point of maximum flexure of the PCB.

4. The system of claim 3, wherein the second MLCC array is oriented to measure all modes of the first vibration.

5. The system of claim 3, wherein the second MLCC array comprises multiple MLCC sensors that are placed at different locations.

6. The system of claim 1, wherein the third MLCC array is positioned near a point of maximum flexure of the PCB.

7. The system of claim 6, wherein the third MLCC array comprises multiple MLCCs that are placed in different orientations.

8. The system of claim 1, wherein the third MLCC array is placed near the first MLCC array.

9. The system of claim 1, wherein the second MLCC array is not a dedicated sensor capacitor array.

10. The system of claim 1, wherein the third MLCC array is not dedicated to generating the second vibration.

11. A system to eliminate an acoustic noise caused by a first electronic component containing piezoelectric material, the system comprising:

the first electronic component containing piezoelectric material, the first component configured to generate a first vibration in response to receiving a varying input voltage, the first vibration causing the acoustic noise;

a second electronic component configured to sense the first vibration and generate a feedback signal;

an adaptive filter configured to use the varying input voltage and the feedback signal from the second MLCC array to generate an output signal; and a third electronic component containing piezoelectric material, the third component configured to use the output signal to generate a second vibration that acts as a counter to dampen the first vibration.

12. The system of claim 11, wherein the adaptive filter continually samples the varying input voltage and the feedback signal to generate the output signal that minimizes the acoustic noise.

13. The system of claim 11, wherein the second electronic component is selected from a group consisting of a strain gauge, a microphone, and an electronic device containing piezoelectric material.

14. The system of claim 11, wherein the first electronic component is positioned on a printed circuit board (PCB).

15. The system of claim 14, wherein the third electronic component is a part of the PCB.

16. A method to eliminate an acoustic noise caused by a first multi-layer ceramic capacitor (MLCC) positioned on a printed circuit board (PCB), the method comprising:

sensing, with a second MLCC, a first vibration and generating a feedback signal, wherein the first vibration is caused by an excitation of the first MLCC in response to receiving a varying input voltage, wherein the first vibration causes the acoustic noise;

generating, by an adaptive filter and using the feedback signal from the second MLCC array, an output signal that is used by a third MLCC to generate a second vibration; and generating, by the third MLCC and using the output signal, the second vibration that acts as a counter to dampen the first vibration.

17. The method of claim 16, wherein generating the output signal comprises: continually sampling, with the adaptive filter, the varying input voltage and the feedback signal to generate the output signal that minimizes the acoustic noise.

18. The method of claim 17, wherein continually sampling the varying input voltage and the feedback signal comprises: periodically sampling, with the adaptive filter, the varying input voltage and the feedback signal at a fixed time interval.

19. The method of claim 18, wherein the varying input voltage changes over time in frequency, phase, and amplitude.

20. The method of claim 19, wherein the adaptive filter is a digital filter.

* * * * *